United States Patent
Yu et al.

(10) Patent No.: US 9,623,554 B2
(45) Date of Patent: Apr. 18, 2017

(54) WEARABLE ROBOT

(71) Applicant: POSCO, Pohang-si (KR)

(72) Inventors: Ho Yu, Pohang-si (KR); Kyung-Lyong Han, Pohang-si (KR); Il-Seop Choi, Pohang-si (KR)

(73) Assignee: POSCO, Pohang-si (KR)

( * ) Notice: Subject to any disclaimer, the term of this patent is extended or adjusted under 35 U.S.C. 154(b) by 143 days.

(21) Appl. No.: 14/591,058

(22) Filed: Jan. 7, 2015

(65) Prior Publication Data

US 2016/0052127 A1 Feb. 25, 2016

(30) Foreign Application Priority Data

Aug. 21, 2014 (KR) .................. 10-2014-0108840

(51) Int. Cl.
*B25J 9/00* (2006.01)
*A61F 2/60* (2006.01)
*A61H 1/02* (2006.01)

(52) U.S. Cl.
CPC ............ *B25J 9/0006* (2013.01); *A61F 2/60* (2013.01); *A61F 2/605* (2013.01); *A61H 1/02* (2013.01); *A61H 1/0237* (2013.01); *Y10S 901/01* (2013.01)

(58) Field of Classification Search
CPC ........ B25J 9/0006; Y10S 901/01; A61H 1/02; A61H 1/0237; A61F 2/60; A61F 2/605
See application file for complete search history.

(56) References Cited

U.S. PATENT DOCUMENTS

| 5,701,948 | A | 12/1997 | Strezov et al. | |
|---|---|---|---|---|
| 7,066,896 | B1 * | 6/2006 | Kiselik | A61H 1/02 601/33 |
| 2006/0260620 | A1 * | 11/2006 | Kazerooni | A61B 5/1038 128/845 |
| 2008/0161937 | A1 * | 7/2008 | Sankai | A61H 3/008 623/25 |
| 2009/0292369 | A1 * | 11/2009 | Kazerooni | B25J 9/0006 623/27 |
| 2011/0066088 | A1 * | 3/2011 | Little | B25J 9/0006 601/35 |
| 2011/0295164 | A1 * | 12/2011 | Jacobsen | A61F 2/68 601/23 |

(Continued)

FOREIGN PATENT DOCUMENTS

KR 2012-0104742 A 9/2012

*Primary Examiner* — Kevin Hurley
*Assistant Examiner* — Marlon R Arce
(74) *Attorney, Agent, or Firm* — The Webb Law Firm (57) ABSTRACT

There is provided a wearable robot able to maintain a balanced state during operations thereof. The wearable robot includes: a wearable robot body; a travel unit for moving the wearable robot body; and a hip joint unit provided in the wearable robot body and coupled to the travel unit, for maintaining a posture of the wearable robot body in response to a movement of the travel unit. With this construction, the wearable robot is provided with a hip joint unit having a resilient force such that a posture of a wearable robot body can be maintained during an operation of the hip joint unit, so that the robot can be operated more stably. Further, because a posture of the wearable robot can be stably maintained so that the safety of the user can be guaranteed and operation efficiency can be improved.

4 Claims, 6 Drawing Sheets

(56) References Cited

U.S. PATENT DOCUMENTS

| | | | | |
|---|---|---|---|---|
| 2012/0271207 A1* | 10/2012 | Schoen | ............... | A61F 5/0102 601/34 |
| 2013/0303950 A1* | 11/2013 | Angold | ................... | A61H 3/00 601/35 |
| 2014/0358053 A1* | 12/2014 | Triolo | ..................... | A61H 3/00 602/16 |
| 2015/0158175 A1* | 6/2015 | Kim | ...................... | B25J 9/0006 700/261 |
| 2015/0351995 A1* | 12/2015 | Zoss | ..................... | A61H 1/024 623/32 |
| 2016/0058647 A1* | 3/2016 | Maddry | ............... | B25J 9/0006 623/26 |

\* cited by examiner

WEARABLE ROBOT

CROSS-REFERENCE TO RELATED APPLICATION

This application claims the benefit of Korean Patent Application No. 10-2014-0108840 filed on Aug. 21, 2014, with the Korean Intellectual Property Office, the disclosure of which is incorporated herein by reference.

BACKGROUND OF THE INVENTION

The present disclosure relates to a wearable robot, and more particularly, to a wearable robot able to maintain a balanced state during operations thereof.

In recent years, wearable robots have been applied to a converter construction process for the construction of a converter in a steel mill. Although refractories may be placed on the bottom and intermediate portions of a converter using light construction equipment, all refractories must be laid by manpower alone, as a piece of light construction equipment cannot be utilized at the cone of the converter. The weight of individual refractories is about 25 to 50 kg, and a construction worker may suffer from a musculoskeletal disease or have an accident over the course of carrying several thousand bricks. In order to address such problems, a wearable robot may be applied to a building process, and handling units may be installed at ends of both arms of the wearable robot to grip and move the refractories.

Figure 1:
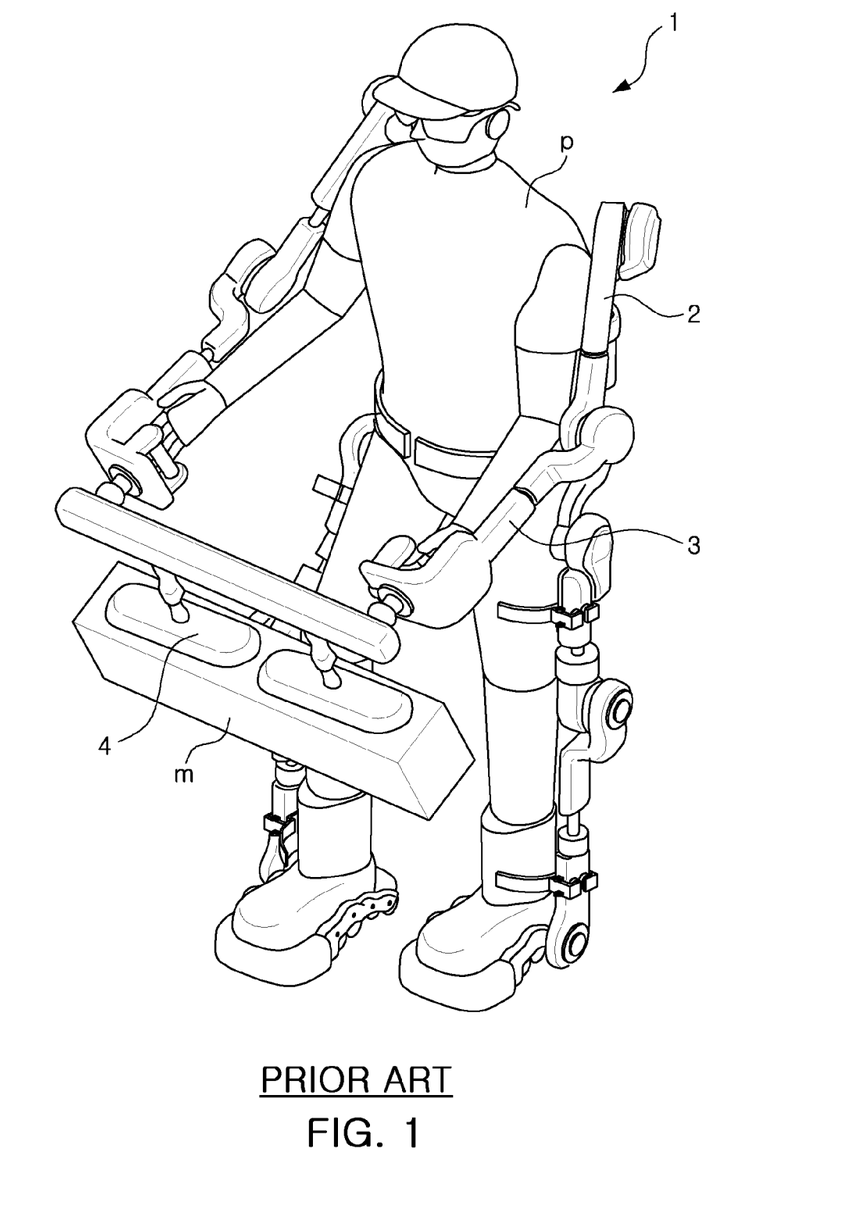
FIG. 1 is a perspective view schematically illustrating a wearable robot including a handling unit according to the related art.

FIG. 1 is a view schematically illustrating a wearable robot.

Referring to FIG. 1, the wearable robot 1 includes a body 2 which may be worn by a user p, and a plurality of joints provided to be moved in response to movements of the user p. Handling units 4 for handling and positioning a refractory m using pneumatic pressure are provided at ends of both arms 3 of the wearable robot 1. With this construction, the refractory m having a relatively heavy weight is absorbed by the handling units 4 and is moved to an installation site to be installed.

However, when such a wearable robot is used, the degree of freedom of joint movement thereof may not as high as that of a human, and there may be limits in terms of lifting, moving, and lowering a refractory. In particular, when a refractory having a relatively heavy weight is carried, the upper limbs are moved as the lower limbs are moved, and thus, the wearable robot maybe frequently unbalanced and may topple over. Further, when the waist or hip is fixed, the upper limbs connected to the lower limbs may be significantly moved if the lower limbs are moved.

Figure 2A:
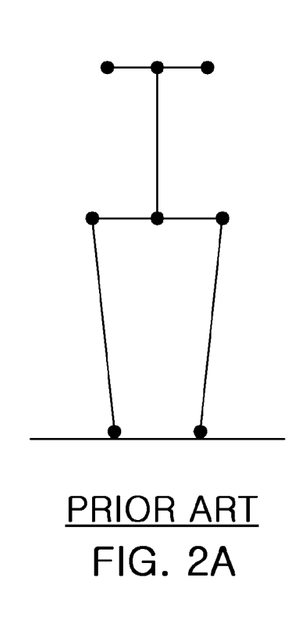
FIGS. 2A, 2B and 2C are diagrams schematically illustrating operational states of the wearable robot according to the related art.
Figure 2B:
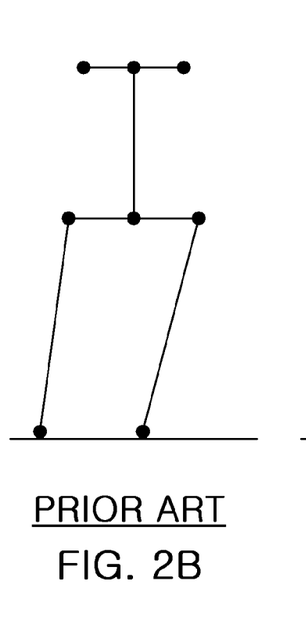
Figure 2C:
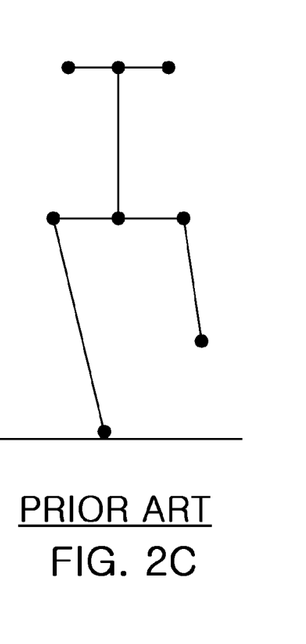

FIGS. 2A, 2B and 2C are diagrams schematically illustrating operational states of a wearable robot. FIG. 2A illustrates a general upright state of the wearable robot, FIG. 2B illustrates an inclined state, and FIG. 2C illustrates a walking state. If the lower limbs are inclined laterally as in FIG. 2B, center of gravity of the wearable robot is moved in a lateral direction and the wearable robot may be unbalanced. When the wearable robot is in a walking state in FIG. 3C, the center of gravity of the wearable robot is moved and the wearable robot may be unbalanced as a whole through being inclined toward a leg opposite to the lifted leg.

As described above, if the leftward and rightward movements of the lower limbs are intentionally limited to prevent the upper limbs of the wearable robot from moving excessively, it is difficult for the center of gravity to be naturally moved to allow for a walking operation to occur.

SUMMARY OF THE INVENTION

An aspect of the present disclosure may provide a wearable robot which is provided with a hip joint unit having a resilient force such that a posture of a wearable robot body can be maintained during operations of the hip joint unit.

According to an aspect of the present disclosure, a wearable robot includes: a wearable robot body; a travel unit for moving the wearable robot body; and a hip joint unit provided in the wearable robot body and coupled to the travel unit, for maintaining a posture of the wearable robot body in response to a movement of the travel unit.

The hip joint unit may include: a plurality of frames to which the travel unit is coupled; and a resilient part coupled to the wearable robot body and coupled between a plurality of frames, for providing resilient force such that the plurality of frames return to an original state.

The resilient part may include: a plurality of link members connecting the plurality of frames and rotatably connected to the plurality of frames; and a resilient member coupling the plurality of link members, for returning the plurality of link members to an original position in the case that the plurality of link members are moved in different directions.

The resilient member may be coupled to the plurality of link members in a direction perpendicular to the plurality of link members.

A plurality of resilient members may be coupled to the plurality of link members.

Any one of the plurality of link members may include a coupling part coupled to the wearable robot body.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION OF THE INVENTION

In order to help understanding of features of the present disclosure, a wearable robot according to an exemplary embodiment of the present disclosure will be described below in detail.

It is to be noted that, when reference numerals are given to the constituent elements of the accompanying drawings to aid in an understanding of the embodiments of the present disclosure, the same constituent elements are denoted by the same reference numerals even if depicted in different drawings. Further, in the following description of the present disclosure, a detailed description of known functions and configurations incorporated herein will be omitted in the case that the subject matter of the present disclosure is rendered unclear thereby.

Hereinafter, the detailed embodiment of the present disclosure will be described with reference to the accompanying drawings.

Figure 3:
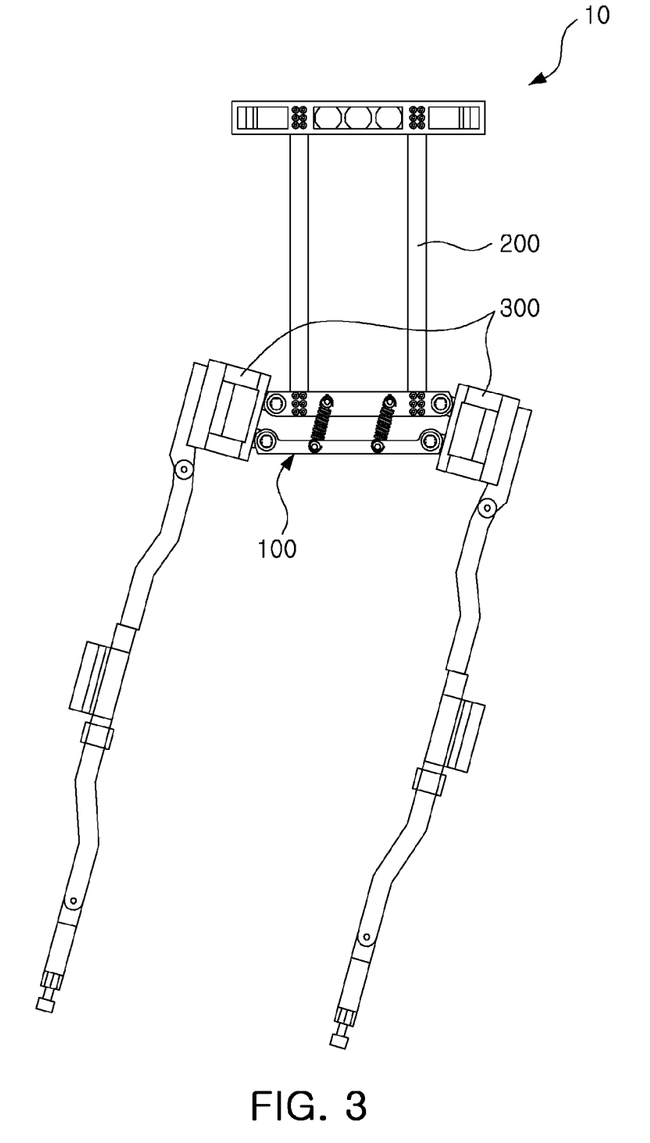
FIG. 3 is a front view schematically illustrating a wearable robot according to an embodiment of the present disclosure.
Figure 4:
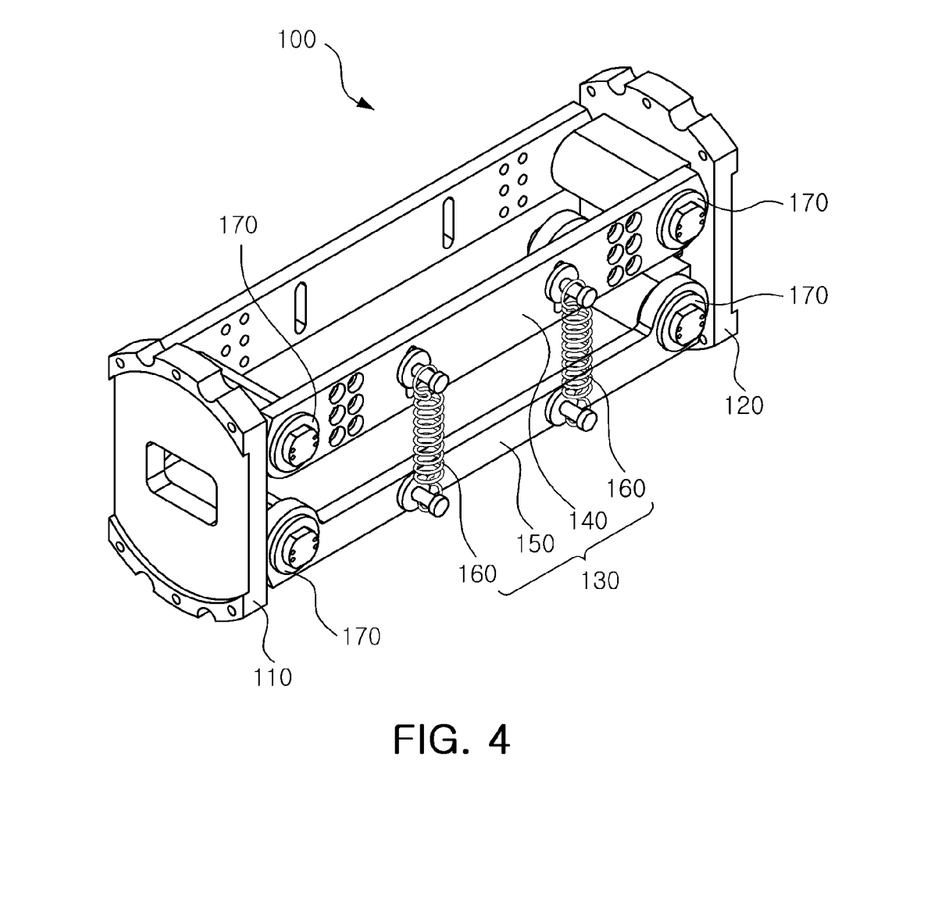
FIG. 4 is a perspective view schematically illustrating a main part of the wearable robot according to the embodiment of the present disclosure.
Figure 5:
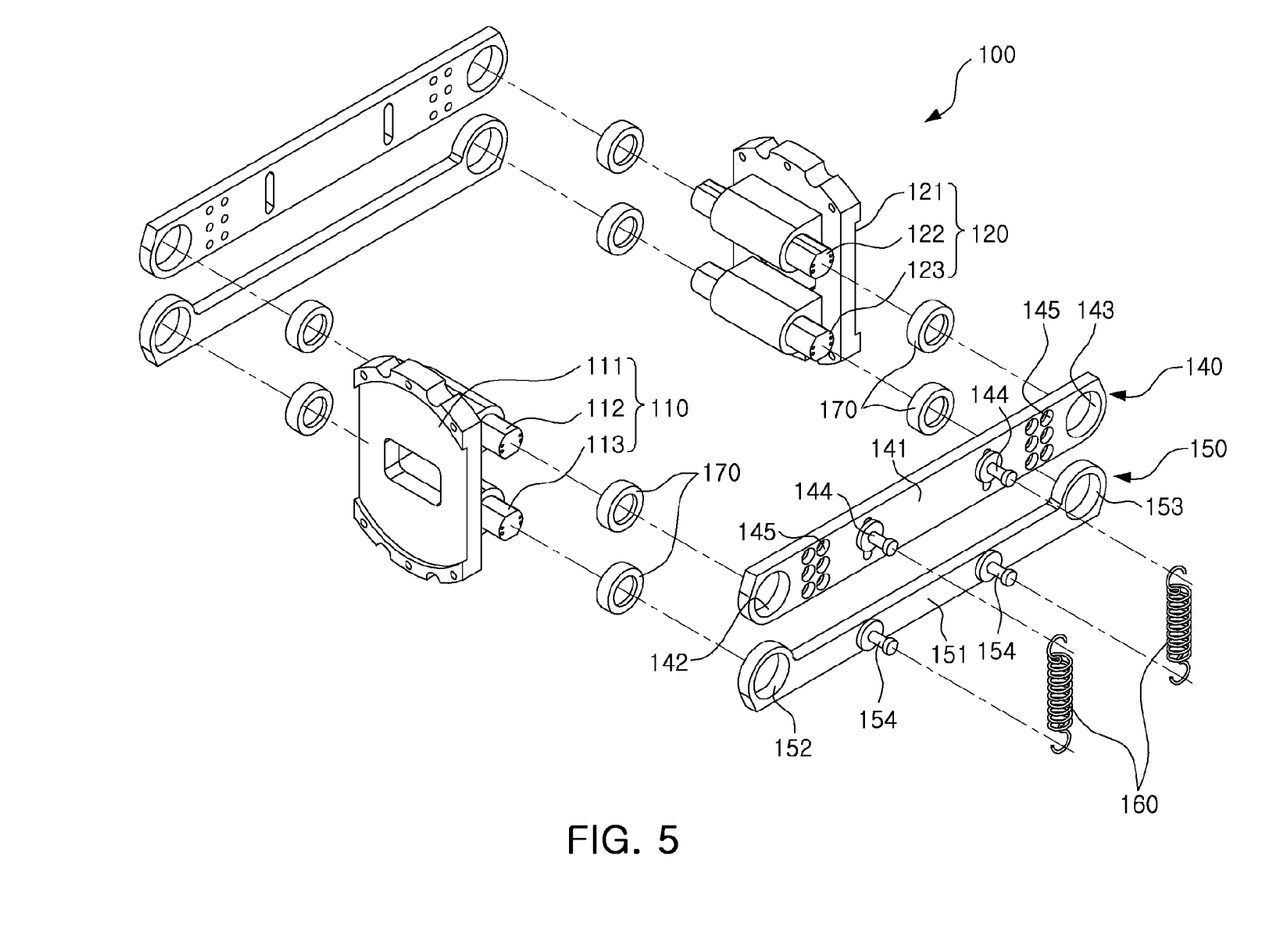
FIG. 5 is an exploded perspective view schematically illustrating the main part of FIG. 4.
Figure 6A:
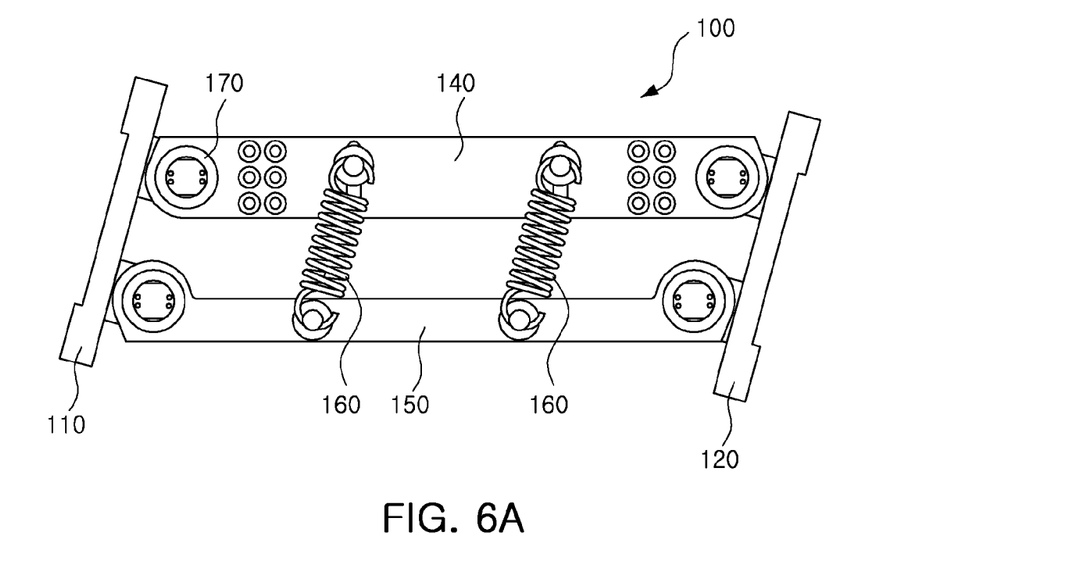
FIG. 6A is a view schematically illustrating a first operational state of the main part of FIG. 4.
Figure 6B:
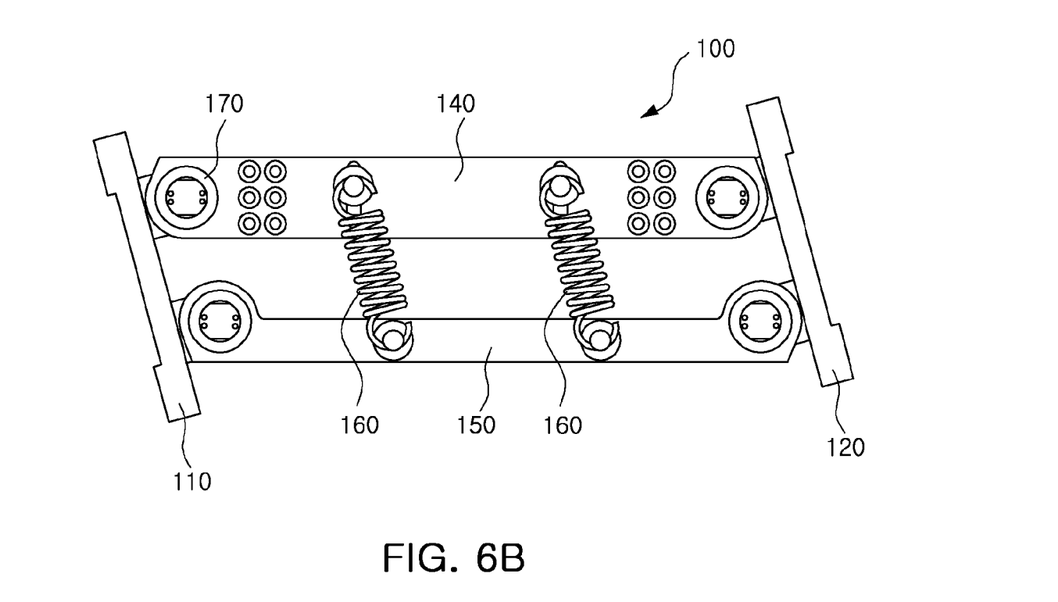
FIG. 6B is a view schematically illustrating a second operational state of the main part of FIG. 4.

FIG. 3 is a front view schematically illustrating a wearable robot including a hip joint unit according to an embodiment of the present disclosure; FIG. 4 is a perspective view schematically illustrating the hip joint unit. FIG. 5 is an exploded perspective view schematically illustrating the hip joint unit. FIGS. 6A and 6B are views illustrating operational states of the hip joint unit.

Referring to FIG. 3, the wearable robot 10 according to the embodiment of the present disclosure includes a wearable robot body 200, a travel unit disposed on opposite sides of the wearable robot body 200, for moving the wearable robot body 200, a hip joint unit 100 provided in the wearable robot body 200 and coupled to opposite sides of the travel unit 300, for maintaining a posture of the wearable robot body 200 in response to a movement of the travel unit 300.

The wearable robot body 200 is provided such that a user can wear the wearable robot. Although FIG. 3 schematically illustrates the wearable robot body 200 such that the main features of the present disclosure may be clearly understood, the wearable robot body 200 is provided such that a user can wear the wearable robot.

The travel unit 300 is installed on opposite sides of the hip joint unit 100, and although not shown in the drawings, the travel unit 300 is configured to be coupled to both legs of the user. Further, a plurality of joint units and a plurality of actuators are provided to be controlled to be operated together when the user walks.

Referring to FIGS. 4 and 5, the hip joint unit 100 includes a first frame 110 and a second frame 120 to which the travel unit 300 is coupled, and a resilient part 130 for providing resilient force to the first frame 110 and the second frame 120.

The first frame 110 is provided to have a flat plate shape, and has a front surface 111 to which the travel unit 300 (see FIG. 3) is coupled, and rotary shafts 112 and 113 provided on a rear surface of the first frame 110 and to which the resilient part 130 is coupled.

The rotary shafts 112 and 113 include a first rotary shaft 112 provided on the upper side and a second rotary shaft 113 provided on the lower side. Of course, the number of rotary shafts is not limited thereto, but may be changed by the user according to necessity.

The second frame 120 has the same shape as that of the first frame 110, which has been described above, and is disposed to be symmetrical to the first frame 110 with respect to the resilient part 130.

The resilient part 130 includes a first link member 140 and a second link member 150 connecting the first frame 110 and the second frame 120 and rotatably connected to the frames 110 and 120, and a resilient member 160 coupling the first link member 140 and the second link member 150. Although two link members are provided on the upper and lower sides to be parallel to each other, the number of link members is not limited thereto and is determined in consideration of the rotary shafts provided in the frame.

The first link 140 includes a link body 141, a first left hole 142 rotatably fitted with the first rotary shaft 112 of the first frame 110, a second right hole 143 rotatably fitted with the second rotary shaft 122 of the second frame 120, and a resilient member support 144 protruding such that one side of the resilient member 160 is coupled to the resilient member support 144. The first link 140 may further include a plurality of wearable robot body coupling parts 145 coupled to the wearable robot body 200 (see FIG. 3).

The second link 150 includes a link body 151, a second left hole 152 rotatably fitted with the second rotary shaft 113 of the first frame 110, a second right hole 153 rotatably fitted with the second rotary shaft 123 of the second frame 120, and a resilient member support 154 protruding such that an opposite side of the resilient member 160 is coupled to the resilient member support 154.

As shown in the drawings, the first link member 140 and the second link member 150 may include a plurality of resilient member supports such that a plurality of resilient members 160 are coupled to the resilient member supports.

It is preferable that the resilient member support 144 of the first link member 140 and the resilient member support 154 of the second link member 150 be disposed in a direction perpendicular to the lengthwise directions of the first link member 140 and the second link member 150.

The first and second frames 110 and 120 and the first and second link members 140 and 150 are rotatably coupled to each other, and bearings 170 are coupled between the rotary shafts 112, 113, 122, and 123 of the first and second frames and the holes 142, 143, 152, and 153 of the first and second link members for smooth relative rotation thereof.

As illustrated in the drawings, the same configurations as the first and second link members 140 and 150 may be further provided in the first and second frames 110 and 120 in a plurality of rows.

With this construction, an operational state of the hip joint unit 110 according to the present disclosure will be described.

FIG. 6 is a view illustrating states in which the hip joint unit 100 is inclined leftwards and rightwards according to a travel state of the wearable robot body. Here, it will be described that the first link 140 is coupled to the wearable robot body and the second link member 150 is moved to the left and right sides of the fixed first link member 140. Although FIG. 6 does not show the travel unit, it will be described as an example that the wearable robot body 200 and the travel unit 300 illustrated in FIG. 3 are coupled to each other.

FIG. 6A illustrates a state in which the right travel unit is supported and the left travel unit is lifted with reference to the drawings. In the operational state, the second link member 150 is moved leftwards and center of gravity of the wearable robot body is moved rightwards such that the first and second frames 110 and 120 are inclined.

In this state, a resilient force of the resilient member 160 coupled between the first link member 140 and the second link member 150 applies a force in a direction in which the second link 150 returns to an original position, and as a result, a force is applied such that the first and second frames 110 and 120 are vertical to the ground surface.

FIG. 6B illustrates a state in which the left travel unit is supported and the right travel unit is lifted with reference to the drawings. In the operational state, the second link member 150 is moved rightwards and center of gravity of the wearable robot body is moved leftwards such that the first and second frames 110 and 120 are inclined.

In the same way, a resilient force of the resilient member 160 applies a force in a direction in which the second link 150 returns to an original position, and as a result, a force is applied such that the first and second frames 110 and 120 are vertical to the ground surface again.

Accordingly, the wearable robot body can be entirely balanced by more smoothly moving center of gravity of the wearable robot body moved by the hip joint unit 100 of the present disclosure.

According to the wearable robot according to the present disclosure, the wearable robot is provided with a hip joint unit having a resilient force such that a posture of a wearable robot body can be maintained during an operation of the hip joint unit, so that the robot can be operated more stably.

According to the present disclosure, because a posture of the wearable robot can be stably maintained so that the safety of the user can be guaranteed and operation efficiency can be improved.

While the present disclosure has been shown and described in connection with the embodiments, it will be apparent to those skilled in the art that modifications and variations can be made without departing from the scope of the invention as defined by the appended claims.

What is claimed is:

1. A wearable robot comprising:
   a wearable robot body;
   a travel unit for moving the wearable robot body; and
   a hip joint unit provided in the wearable robot body and coupled to opposite sides of the travel unit, for maintaining a posture of the wearable robot body in response to a movement of the travel unit,
   wherein the hip joint comprises:
   a first frame and a second frame, to which the travel unit is coupled; and
   a resilient part coupled to the wearable robot body and coupled between the first frame and the second frame, for providing resilient force such that the first frame and the second frame return to an original state,
   wherein the resilient part comprises:
   a plurality of link members connecting the first frame and the second frame and rotatably connected to the first frame and the second frame, and provided to be parallel to each other; and
   a resilient member coupling the plurality of link members, for returning the plurality of link members to an original position in the case that the plurality of link members are moved in different directions.

2. The wearable robot of claim 1, wherein the resilient member is coupled to the plurality of link members in a direction perpendicular to the plurality of link members.

3. The wearable robot of claim 2, wherein a plurality of resilient members are coupled to the plurality of link members.

4. The wearable robot of claim 1, wherein any one of the plurality of link members comprises a coupling part coupled to the wearable robot body.

* * * * *

UNITED STATES PATENT AND TRADEMARK OFFICE
CERTIFICATE OF CORRECTION

PATENT NO. : 9,623,554 B2
APPLICATION NO. : 14/591058
DATED : April 18, 2017
INVENTOR(S) : Ho Yu et al.

It is certified that error appears in the above-identified patent and that said Letters Patent is hereby corrected as shown below:

On the Title Page

Column 2, Assistant Examiner, delete "Marlon R Arce" and insert -- Marlon A Arce --

Signed and Sealed this
Sixth Day of June, 2017

Michelle K. Lee
*Director of the United States Patent and Trademark Office*